United States Patent [19]

Margolis-Nunno et al.

[11] Patent Number: 6,087,141
[45] Date of Patent: Jul. 11, 2000

[54] PROCESS FOR THE STERILIZATION OF BIOLOGICAL COMPOSITIONS AND THE PRODUCT PRODUCED THEREBY

[75] Inventors: Henrietta Margolis-Nunno; Ehud Ben-Hur; Bernard Horowitz, all of New York, N.Y.

[73] Assignee: New York Blood Center, Inc., New York, N.Y.

[21] Appl. No.: 09/128,749

[22] Filed: Aug. 4, 1998

Related U.S. Application Data

[60] Continuation of application No. 08/725,594, Oct. 3, 1996, Pat. No. 5,789,150, which is a division of application No. 08/344,919, Nov. 25, 1994, Pat. No. 5,658,722, which is a continuation-in-part of application No. 08/069,235, May 28, 1993, abandoned, which is a continuation-in-part of application No. 08/031,787, Mar. 15, 1993, abandoned, which is a division of application No. 07/706,919, May 29, 1991, Pat. No. 5,232,844, which is a continuation-in-part of application No. 07/524,208, May 15, 1990, Pat. No. 5,120,649.

[51] Int. Cl.[7] .............................. C12N 13/00; C12N 7/04; A01N 63/00
[52] U.S. Cl. .................................... 435/173.3; 435/173.1; 435/236; 424/93.72
[58] Field of Search .............................. 435/173.1, 173.3, 435/236; 424/93.21, 93.72

[56] References Cited

U.S. PATENT DOCUMENTS

| | | | |
|---|---|---|---|
| 4,493,981 | 1/1985 | Wiesehahn et al. | 435/238 |
| 5,120,649 | 6/1992 | Horowitz et al. | 435/173.1 |
| 5,232,844 | 8/1993 | Horowitz et al. | 435/173.1 |
| 5,658,722 | 8/1997 | Margolis-Nunno et al. | 435/2 |
| 5,789,150 | 8/1998 | Margolis-Nunno et al. | 435/2 |

OTHER PUBLICATIONS

Beer et al., Photochem. Photobiol., 59(6), "Reassessment of the Differential Effects of Ultraviolet and Ionizing Radiation on HIV Promoter—The Use of Cell–Survival as the Basis for Comparisons", pp. 643–649, 1994.

Keeton et al., Biological Science, 4th Ed., W.W. Norton & Co., New York, p. 346, 1986.

Guttman, Dermatology Times, UVA–Induced Anuclear Damage Seen in Mammalian Blood Cells, p. 64, full text from PROMT, Nov. 1991.

Lin et al., Blood, 74, "Use of 8–Methoxypsoralen and Long–Wavelength Ultraviolet Radiation for Decontaminationg of Platelet Concentrates", pp. 517–525, 1989.

*Primary Examiner*—Jon P. Weber
*Attorney, Agent, or Firm*—Amster, Rothstein & Eberstein

[57] ABSTRACT

The present invention concerns a process for inactivating extracellular and intracellular virus in a biological composition without incurring substantial disruption or inactivation thereof, said process comprising subjecting said composition to a virucidally effective amount of UVA1 irradiation substantially in the absence of UVA2 irradition for a period of time sufficient to thereby inactivate said virus while retaining functionality of said composition. The biological composition is advantageously a product that contains red blood cells or platelets. The process is advantageously carried out in the presence of an irradiation sensitizer compound and/or a quencher. The present invention also concerns the product substantially identical to that produced bythe inventive process.

13 Claims, 3 Drawing Sheets

PROCESS FOR THE STERILIZATION OF BIOLOGICAL COMPOSITIONS AND THE PRODUCT PRODUCED THEREBY

CROSS-REFERENCE TO RELATED APPLICATIONS

This application is a continuation of U.S. application Ser. No. 08/725,594, filed Oct. 3, 1996, now issued as U.S. Pat. No. 5,789,150, which is, in turn, a divisional of U.S. application Ser. No. 08/344,919, filed Nov. 25, 1994, now issued as U.S. Pat. No. 5,658,722, which is, in turn, a continuation-in-part of U.S. application Ser. No. 08/069,235, filed May 28, 1993, now abandoned, which is, in turn, a continuation-in-part of U.S. application Ser. No. 08/031,787, filed Mar. 15, 1993, now abandoned, which is, in turn, a divisional of U.S. application Ser. No. 07/706,919, filed May 29, 1991, now issued as U.S. Pat. No. 5,232,844, which is in turn a continuation-in-part of U.S. application Ser. No. 07/524,208, filed May 15, 1990, now issued as U.S. Pat. No. 5,120,649.

GOVERNMENT RIGHTS

This work is supported in part by award No. ROI-HL 41221 from the National Heart, Lung and Blood Institute.

BACKGROUND OF THE INVENTION

1. Field of the Invention

The present invention concerns a process for rendering a biological composition substantially free of enveloped and non-enveloped viruses contained therein without substantial disruption or inactivation of cells contained therein and without significant loss of labile proteins or other valuable biological components also contained therein.

2. Description of Related Art

The problems associated with the application of virucidal procedures to biological compositions and the efforts to date to overcome these problems, including the application of light and chemical agents is reviewed briefly in U.S. Pat. Nos. 5,232,844 and 5,120,649, the disclosures of which are incorporated herein by reference. See column 1, line 26, through column 4, line 43, of U.S. Pat. No. 5,232,844 and column 1, line 27, through column 4, line 41, of U.S. Pat. No. 5,120,649.

Various photodynamic sterilization techniques have been evaluated for inactivating viruses in cellular components of blood. Although many of these appear promising for the treatment of red cell concentrates (Matthews et al., "Photodynamic therapy of viral contaminants with potential for blood banking applications", in *Transfusion*, 28:81–83 (1988); O'Brien et al., "Evaluation of merocyanine 540-sensitized photoirradiation as a means to inactivate enveloped viruses in blood products", in *J. Lab. Clin. Med.*, 116:439–47 (1990); and Horowitz et al., "Inactivation of viruses in blood with aluminum phthalocyanine derivatives", in *Transfusion*, 31:102–8 (1991)), photodynamic viral inactivation methods involving solely oxygen dependent reactions have so far proved inappropriate for the treatment of platelet concentrates (Proudouz et al., "Inhibition by albumin of merocyanine 540-mediated photosensitization of platelets and viruses", in *Transfusion*, 31:415–22 (1991), Dodd et al., "Inactivation of viruses in platelet suspensions that retain their in vitro characteristics: comparison of psoralen-ultraviolet A and merocyanine 540-visible light methods", in *Transfusion*, 31:483–90 (1991); and Horowitz et al., "Inactivation of viruses in red cell and platelet concentrates with aluminum phthalocyanine (AlPc) sulfonates", in *Blood Cells*, 18:141–50 (1992)).

The use of psoralens together with UVA has demonstrated promise as a means of photoinactivating viral contaminants in platelet concentrates, although in most studies (Lin et al., "Use of 8-methoxypsoralen and long-wavelength ultraviolet radiation for decontamination of platelet concentrates", in *Blood*, 74:517–525 (1989); and Dodd et al., supra, aminomethyl-trimethylpsoralen (AMT)), the combination of high levels of virus inactivation and the maintenance of platelet function were possible only when air was exchanged with nitrogen prior to UVA irradiation, a cumbersome procedure with inherent variability.

However, it was recently demonstrated (Margolis-Nunno et al., "Virus Sterilization in Platelet Concentrates with Psoralen and UVA in the Presence of Quenchers" *Transfusion*, 22:541–547 (1992)), that for the inactivation of $\geq 6.0$ $\log_{10}$ cell-free vesicular stomatitis virus (VSV) by AMT and UVA, the need for oxygen depletion as a means of protecting platelets could be obviated by inclusion of mannitol, a scavenger (quencher) of free radicals. (The addition of quenchers of type I (free radical mediated) or of type II (singlet oxygen mediated) photodynamic reactions is frequently used in other contexts to distinguish which active oxygen species produces a particular photodynamic effect.) Under the conditions used in that study, i.e., 25 μg/ml AMT and 30 minutes of UVA with 2 mM mannitol, the inactivation of cell-free VSV in air was in part oxygen dependent since equivalent virus kill ($\geq 6.0$ $\log_{10}$) with oxygen depleted required 3 to 4 times more UVA irradiation time (90 minutes to 2 hours).

However, while these methods achieved a high level of kill of cell-free lipid enveloped viruses, non-enveloped viruses and latent actively replicating and cell-associated viruses were not killed to a high extent under the conditions reported therein. Therefore, there was the need to effect the kill of these latter virus forms without causing significant damage to the desired, valuable components in the biological mixture. Conditions which result in the kill of $\geq 10^6$ infectious doses of latent or non-enveloped virus have been shown to modify red blood cells and platelets and result in compromised recovery of labile proteins such as factor VIII.

In our copending application Ser. No. 08/069,235, the entire contents of which are hereby incorporated by reference, we demonstrated that superior viral inactivation could be achieved at the same time that superior protection of cells and labile proteins was also achieved by subjecting the biological composition, e.g., platelet concentrates to a virucidally effective amount of irradiation in the presence of (a) a mixture of a compound that quenches type I photodynamic reactions and a compound that quenches type II photodynamic reactions or (b) a bifunctional compound that is capable of quenching both type I and type II reactions for a period of time sufficient to inactivate any virus contained therein.

In spite of these advances, there continues to be a need for novel methods that achieve an even higher level of kill of both enveloped and non-enveloped viruses without significant loss of labile proteins or other valuable biological components.

SUMMARY OF THE INVENTION

The overall objective of the present invention was to achieve a high level of inactivation of both enveloped and non-enveloped viruses in biological compositions without incurring substantial disruption or inactivation of cells meant to be contained therein and without significant loss of labile proteins or other valuable biological components also contained therein. This objective was satisfied with the present invention, which relates generally to a process for inactivating extracellular and intracellular virus in a biological composition without incurring substantial disruption or inactivation thereof, said process comprising subjecting said composition to a virucidally effective amount of UVA1 irradiation alone or in the presence of an irradiation sensitizer compound for a period of time sufficient to inactivate any virus contained in said composition while retaining functionality of said composition. The inventive process can, thus, be used to inactivate viruses in whole blood, red blood cell concentrates and platelet concentrates, without adversely affecting red blood cell or platelet structure or function. Similarly, the inventive process can be used to inactivate viruses in biological compositions without incurring substantial inactivation of desired, soluble biological substances (e.g., coagulation factor concentrates, hemoglobin solutions) contained therein.

We have found that relatively more damage to cells and labile proteins is caused by shorter UVA wavelengths (<350 nm) and, therefore, cells and labile proteins can be better protected by using lamps that do not emit these shorter wave lengths or filters that eliminate these shorter wave lengths, yet viral inactivation levels are not compromised.

In accordance with another aspect of the invention, the inventive process is advantageously carried out in the presence of quencher compound. The quencher compound will be capable of quenching type I or type II photodynamic reactions or both, but preference is given to the use of (a) mixtures of a compound that quenches type I photodynamic reactions with a compound that quenches type II photodynamic reactions or (b) bifunctional compounds capable of quenching both type I and type II reactions.

In accordance with still another aspect of the invention, the inventive process is advantageously combined with a different virucidal method to enhance virus inactivation.

UV treatment alone of either plasma or AHF concentrates results in a relatively high loss of coagulation factor activity under conditions which kill $\geq 10^5$ ID$_{50}$ of virus; however, it has been discovered that this loss is significantly reduced (i.e., the recovery is high) when quenchers of photodynamic reactions are added prior to UV treatment. Compare, Murray et al., "Effect of ultraviolet radiation on the infectivity of icterogenic plasma", in *JAMA*, 157:8–14 (1955); and, more recently, Kallenbach et al., "Inactivation of viruses by ultraviolet light" in Morgenthaler J-J ed. "Virus inactivation in plasma products", in *Cum stud Hematol Blood Transfus.*, 56:70–82 (1989). Thus, the combined treatment according to the present invention results in a very high level of virus kill while coagulation factor activity is retained at high levels.

BRIEF DESCRIPTION OF THE DRAWINGS

FIG. 1 comprises two graphs depicting the effect of UVA wavelength spectrum on psoralen and UVA (PUVA) treated PCs: Treatment of platelet concentrates (PCs) was with 50 μg/ml AMT, 0.35 mM rutin and indicated dose of irradiation using a transilluminator (Spectroline; Model TR 365A) equipped with six 15 watt fluorescent tubes (BLEIT151; Spectroline, Westbury N.Y.) for UVA (320–400 nM; open symbols; 7 mW/cm$^2$), and adding a cut-off filter (WG345, Schott Glass Inc., Duryea Pa.) for UVA1 (345–400 nm; filled symbols; 3.5 mW/cm$^2$).

DETAILED DESCRIPTION OF THE INVENTION

Figure 1A:
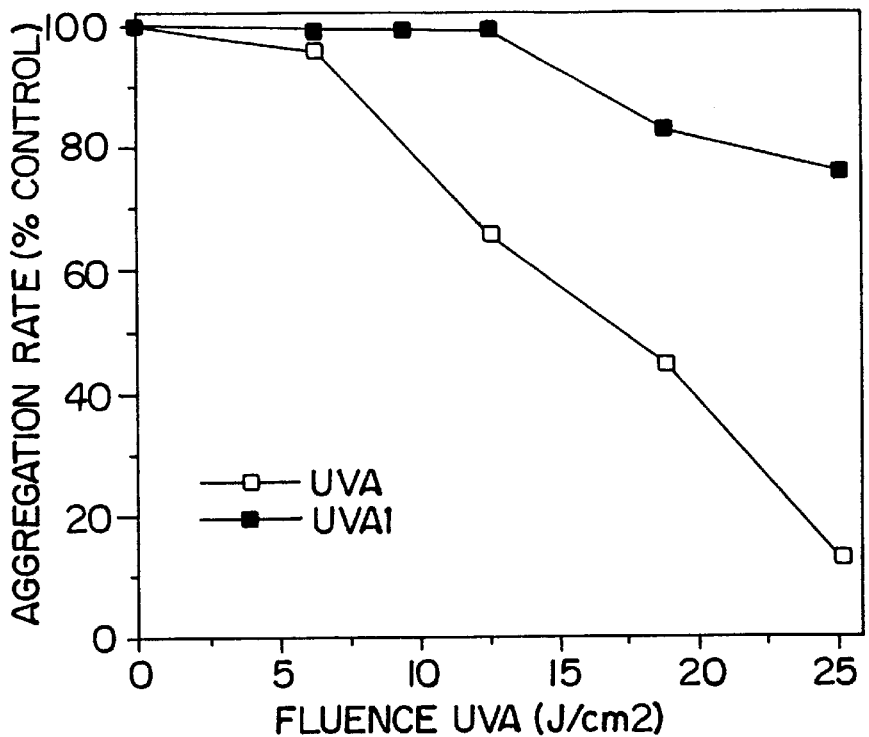
FIG. 1a depicts the rate of platelet aggregation in response to 20 μg/ml collagen as measured after overnight storage following treatment and compared to that of untreated control.

Details regarding the make-up of blood, the usefulness of blood transfusions, cell-types found in blood and proteins found in blood are set forth at column 6, lines 8–51, of U.S. Pat. No. 5,232,844. Techniques regarding blood plasma fractionation are generally well known to those of ordinary skill in the art and an excellent survey of blood fractionation also appears in *Kirk-Other's Encylopedia of Chemical Technology*, Third Edition, Interscience Publishers, Volume 4, pages 25 to 62, the entire contents of which are incorporated by reference herein.

The present invention is directed to subjecting a biological composition such as whole blood, red blood cell concentrates, platelet concentrates, platelet extracts, leukocyte concentrates, semen, ascites fluid, milk, lymphatic fluid, hybridoma cell lines and products derived from any of the above, to UVA irradiation alone or in the presence of an irradiation sensitizer compound and, optionally in the presence of a quencher or a mixture of quenchers.

The terms "cell-containing composition", "biological composition", or "biological fluid", as used herein, are not to be construed to include any living organism. Instead, the inventive method is intended to be carried out in an in vitro environment and the cell-containing composition, biological composition, or biological fluid obtained by the inventive method will, therefore, be an in vitro produced product, but will be usable in vivo.

The present invention can be employed to treat the product of a composition containing non-blood normal or cancerous cells or the product of gene splicing.

The term "UVA1" irradiation, as used herein, is intended to mean UVA light of a wave length ranging from about 340 to 400 nm. The term "UVA", as used herein, is ordinarily intended to refer to UVA light having a broader (320–400 nm) emission spectrum, i.e., including so-called "UVA2" irradiation, which is by convention UVA light of a wavelength ranging from about 320 to 340 nm.

Details on the application of UVA (or UVA1) radiation to effect virus inactivation are well known to those skilled in the art. Typical radiation fluences range for the invention are approximately 0.5–100 J/cm$^2$ (preferably 1–50 J/cm$^2$).

When utilized, suitable quenchers are any substances known to react with both free radicals (so-called "type I quenchers") and reactive forms of oxygen (so-called "type II quenchers"). Representative quenchers include unsaturated fatty acids, reduced sugars, cholesterol, indole derivatives, and the like, azides, such as sodium azide, tryptophan, polyhydric alcohols such as glycerol and mannitol, thiols such as glutathione, superoxide dismutase, flavonoids, such as quercetin and rutin, amino acids, DABCO, vitamins such as vitamin A, C and E and the like.

The quencher is used in conventional quenching amounts, but, surprisingly, when used, the overall process results in preferential damage to the virus but not to the desired biological material.

In accordance with the present invention, superior virus kill is achieved by quenching both type I and type II photodynamic reactions, i.e., by using a mixture of type I and type II quenchers or by using compounds, e.g., flavonoids, that are known to quench both type I and type II reactions. The range of virus kill is in most cases broader than that achieved by using type I or type II quenchers alone—even as compared to increased concentrations of the type I or type II quencher—or by using mixtures of type I quenchers or mixtures of type II quenchers. Moreover, this broader range of virus kill is achieved without sacrificing intact cell functionality or structure.

The inventive process is typically carried out over a temperature range of 0–42° C., preferentially 15–37° C. and most preferentially 15–25° C. The inventive process is typically carried out at pH 6.5–8, most preferentially 7.2–7.6. Samples are typically subjected to the inventive process for a period of time of less than 24 hours. Samples can also be treated frozen.

In an embodiment of the present invention, the biological composition is subjected to irradiation and the quencher or quencher mixture in the presence of an irradiation sensitizer. In this context, suitable irradiation sensitizer compounds for use in the present invention include phthalocyanines, purpurins, and other molecules which resemble the porphyrins in structure (as described above) as well as photoactive compounds excited by ultraviolet light (e.g., psoralen, 8-methoxypsoralen, 4'-aminomethyl-4,5',8-trimethyl psoralen, bergapten, and angelicin), dyes which absorb light in the visible spectrum (e.g., hypericin, methylene blue, eosin, fluoresceins and flavins), and dyes which absorb X-irradiation (e.g. brominated psoralen, brominated hematoporphyrin, iodinated phthalocyanine). The use of such irradiation sensitizers would be readily apparent to those skilled in the art and is preferably substantially as described in U.S. Pat. No. 5,120,649 and U.S. Ser. No. 07/706,919, filed May 29, 1991, the entire disclosures of which are incorporated herein by reference.

According to another embodiment of the invention, the treatment of the biological composition with irradiation and quencher or quencher mixture is combined with a second virucidal method. This second virucidal method can be any method used conventionally to inactivate enveloped and/or non-enveloped viruses such as, merely for example, heat treatment, dry or otherwise, pH manipulation, treatment with lipid solvents and/or detergents, a separate irradiation treatment, e.g., with gamma-irradiation, or treatment with chemical agents, e.g., formaldehyde.

Non-limiting examples of lipid coated, human pathogenic viruses that can be inactivated by the present invention include vesicular stomatitis virus (VSV), Moloney sarcoma virus, Sindbis virus, human immunodeficiency viruses (HIV-1; HIV-2), human T-cell lymphotorophic virus-I (HTLV-I), hepatitis B virus, non-A, non-B hepatitis virus (NANB) (hepatitis C), cytomegalovirus, Epstein Barr viruses, lactate dehydrogenase elevating virus, herpes group viruses, rhabdoviruses, leukoviruses, myxoviruses, alphaviruses, Arboviruses (group B), paramyxoviruses, arenaviruses and coronaviruses. Non-limiting examples of non-enveloped viruses that can be inactivated by the present invention include parvovirus, polio virus, hepatitis A virus, enteric non-A, non-B hepatitis virus, bacteriophage M13 and satellite adeno-associated virus (AAV).

Cell-containing compositions to be treated according to the invention have $\geq 1\times 10^8$ cells/ml, preferably $\geq 1\times 10^9$ cells/ml and most preferably $\geq 1\times 10^{10}$ cells/ml. Furthermore, cell-containing compositions to be treated according to the invention have preferably >4 mg/ml protein and more preferably >25 mg/ml protein and most preferably 50 to 60 mg/ml protein (unwashed cells).

Non-cell containing compositions to be treated according to the invention have $\geq 0.1$ mg/ml and preferably $\geq 5$ mg/ml protein.

In the inventive process, at least $10^4$, preferably $10^6$, infectious units of virus parasite or other pathogen are inactivated.

The biological compositions treated according to the invention, while initially containing $\geq 1000$ infectious units of virus/L, after the virus has been inactivated and treatment according to the invention has been conducted, have, in the case of cell-containing compositions, a retention of intact cell functionality and structure of greater than 70%, preferably greater than 80% and most preferably greater than 95%. In the case of biological fluids, a retention of biological activity of greater than 75%, preferably greater than 85%, and most preferably greater than 95% can be achieved.

By the inactivation procedure of the invention, most if not virtually all of the viruses contained therein would be inactivated. A method for determining infectivity levels by inoculation into chimpanzees (in vivo) is discussed by Prince, A. M., Stephen, W., Bortman, B. and van den Ende, M. C., "Evaluation of the Effect of Beta-propiolactone/Ultraviolet Irradiation (BPL/UV) Treatment of Source Plasma on Hepatitis Transmission by Factor IX Complex in Chimpanzees", *Thrombosis and Hemostasis,* 44: 138–142, (1980).

According to the invention, inactivation of virus is obtained to the extent of at least "4 logs", preferably $\geq 6$ logs, i.e., virus in the sample is totally inactivated to the extent determined by infectivity studies where that virus is present in the untreated sample in such a concentration that even after dilution to $10^4$ (or $10^6$), viral activity can be measured.

The present invention describes inactivating viruses, while simultaneously retaining labile blood cell functional and structural features.

Functional activities of red cells are ascertained by measurements of metabolite levels, enzymatic activities, electrolyte levels and oxygen carrying capacity. Structural integrity of red cells is assessed by measurements of hemoglobin release, osmotic fragility, survival in vivo following radiolabeling with chromium-51, antigenicity and by evaluation of modification of cell surface proteins. Further evidence of the integrity of treated red blood cells comes from the measurement of their circulatory half-life.

While those skilled in the art will appreciate that the inventive process will be useful to sterilize most blood products, including, but not limited to, whole blood, red blood cell concentrates, platelet concentrates, platelet extracts, leukocyte extracts, blood protein concentrates, etc., the inventive method will prove especially valuable for the sterilization of platelet concentrates and platelet extracts. As alluded to previously, there is a special need for sterilization processes that afford superior viral inactivation while at the same time being protective of platelets. The present invention satisfies this need.

Functional activities of platelets are determined by their ability to aggregate in the presence of certain biological agents and their morphology and, also, by assessing the maintenance of the pH upon limited storage of a solution containing the platelets and in vivo hemostatic effectiveness using the rabbit ear bleeding time technique (Wagner et al., 1993, *Blood,* 82:3489. Structural integrity of platelets is assessed by in vivo survival following radiolabeling with indium-111 and identification of the presence of specific platelet antigens.

After treatment with the photoreactive compound, excess photoreactive compound can be removed by centrifugation, washing dialysis, and/or adsorption onto hydrophobic matrices.

In an embodiment of the present invention, the treated cell-containing fraction from the inventive process is transfused or returned to the donor, e.g., human donor, from which the initial cell-containing fraction was derived. In this manner, the level of circulating virus in the donor will be reduced, thus improving the donor's ability to clear virus and/or improving the efficacy of antiviral drugs.

Factor VIII and factor IX coagulant activities are assayed by determining the degree of correction in APTT time of factor VIII—and factor IX—deficient plasma, respectively. J. G. Lenahan, Philips and Philips, *Clin. Chem.,* Vol. 12, page 269 (1966).

The activity of proteins which are enzymes is determined by measuring their enzymatic activity. Factor IX's activity can be measured by that technique.

Binding proteins can have their activities measured by determining their kinetics and affinity of binding to their natural substrates.

Lymphokine activity is measured biologically in cell systems, typically by assaying their biological activity in cell cultures.

Protein activity generally is determined by the known and standard modes for determining the activity of the protein or type of protein involved.

The invention will now be described with reference to the following non-limiting examples.

EXAMPLES

Materials and Methods

Platelet Concentrates (PCs)

PCs, released after routine blood bank testing, were typically 24 to 48 hours old when treated. Prior to treatment, the PCs were stored at 22 to 24° C. in the bags (PL 732, Fenwal Laboratories, Deerfield, Ill.) in which they were received and constantly agitated on a platelet rotator (Helmer Labs, St. Paul, Minn.).

Psoralen Solutions

4'-aminomethyl-4,5',8-trimethylpsoralen (AMT) was purchased from HRI Assoc. Inc., Concord, Calif. Stock solutions of AMT (4 mg/ml) were prepared in distilled water.

Model Virus Studies

The inactivation of vesicular stomatitis virus (VSV), a lipid enveloped, RNA virus was studied.

VSV was cultured in human A549 cells. Culturing and assay procedures were similar to those described in Horowitz, B., Wiebe, M. E., Lippin, A. and Stryker, M. H., "Inactivation of Viruses in Labile Blood Derivatives", *Transfusion,* 1985, 25:516–522. Infectivity of VSV was assessed by endpoint, 10-fold serial dilutions in DMEM culture medium (Gibco Laboratories, Grand Island, N.Y.) with 10% fetal calf serum (FCS; MA Bioproducts, Walkersville, Md.). Each dilution was used to inoculate eight replicate wells of human A549 cells in 96-well microtiter plates. Virus-induced cytopathology was scored after 72 hours of incubation at 37° C. in 5% $CO_2$. The reported virus titer was calculated using the Spearman-Karber method (Spearman, C., "The Method of Right and Wrong Cases' ('Constant Stimuli') Without Gauss's Formula", *Br. J. Psychol.,* 1908;2:227–242) and indicates the quantity of virus which infects 50% of the tissue culture wells ($TCID_{50}$).

For assessment of platelet function, measurement was made of the rate of platelet aggregation (% control) in response to the addition of 20 μm/ml of collagen.

For assessment of virus inactivation, the virucidal reaction was stopped by 10-fold dilution into DMEM containing 5% fetal calf serum, and the cells when present were removed by centrifugation at 1500 rpm for 10 minutes. The lack of virus inactivation at this dilution or in the absence of irradiation was confirmed for each of the inactivation conditions studied. Samples were sterile filtered (Swinnex filters, Millipore Corp., Bedford, Mass.) and frozen at −70° C. or below until assay.

RESULTS

In order to assess the effect on viral specificity of PUVA treatments, i.e., viral kill versus platelet function, we compared the effects of different UVA lamps and filters on identical samples under otherwise similar viral inactivation conditions (e.g., 50 μg/ml AMT, 0.35 mM rutin and 39 $J/cm^2$). In one set of experiments, a fluorescent lamp with a broader UVA emission spectrum ranging over 320–400 nm (UVA) was used, whereas in the second set of experiments, there was used a filter which cut-off wavelengths below 345 nm.

Figure 1B:
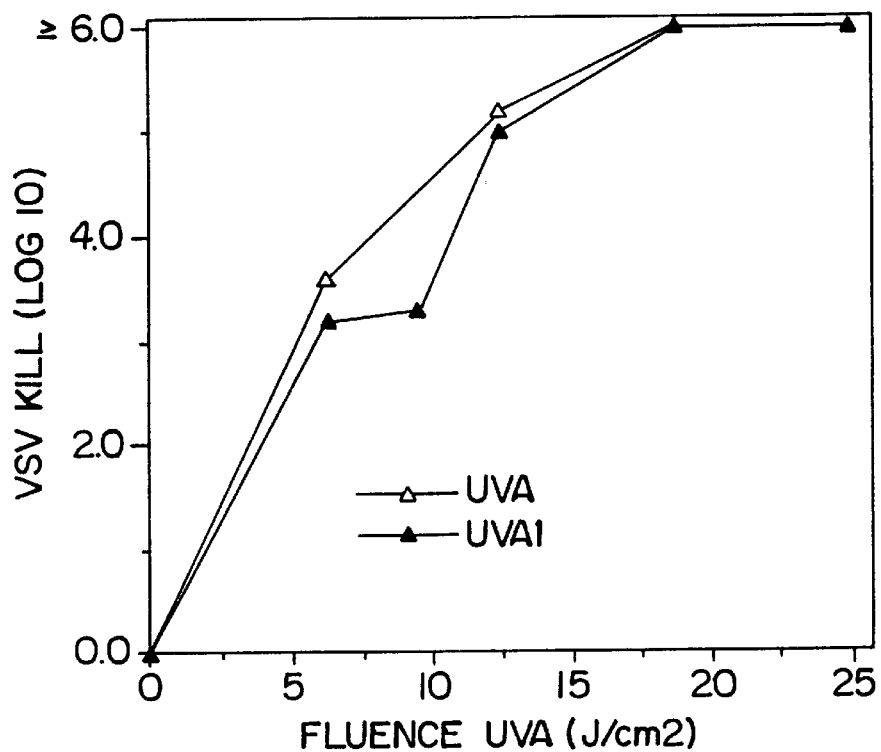
FIG. 1b depicts the results when cell-free VSV was added prior to treatment and infectivity measured after PUVA treatment.
Figure 2:
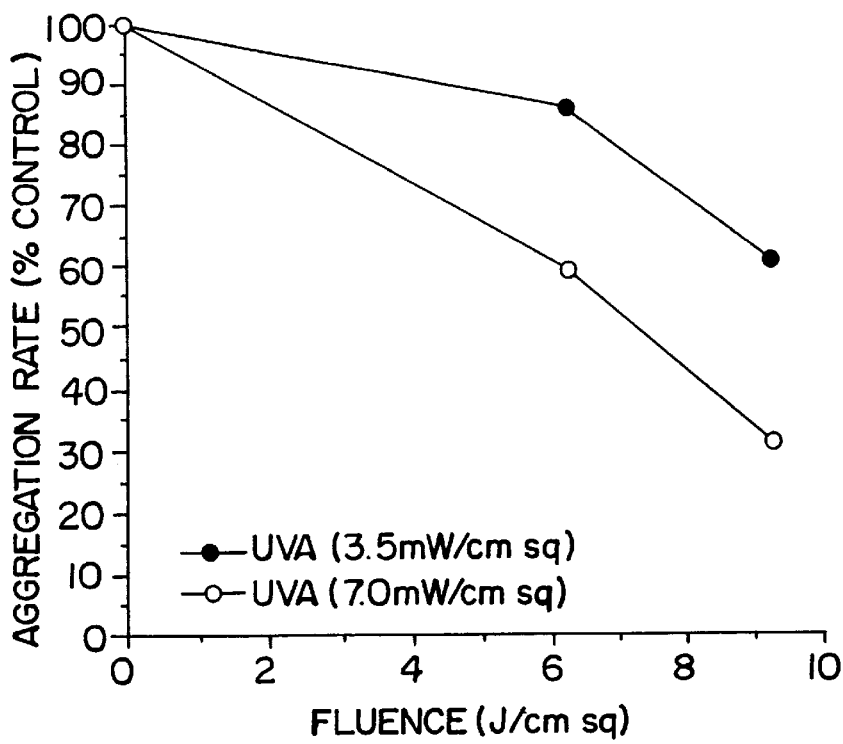
FIG. 2 is a graph depicting the effect of UVA wavelength on treatment in the absence of quenchers: PCs were treated with 50 μg/ml AMT and UVA and UVA1 as in FIG. 1 in the absence of rutin. The rate of platelet aggregation in response to collagen was measured as in FIG. 1.

The results show that, while virus kill was equivalent with equal doses of UVA1 or UVA, platelet function surprisingly was significantly better maintained with UVA1 than with UVA (see FIG. 1). This was also true for PUVA treatment in the absence of rutin or other quenchers (see FIG. 2) where the use of a filter had a positive effect on platelet aggregation after treatment.

Figure 3:
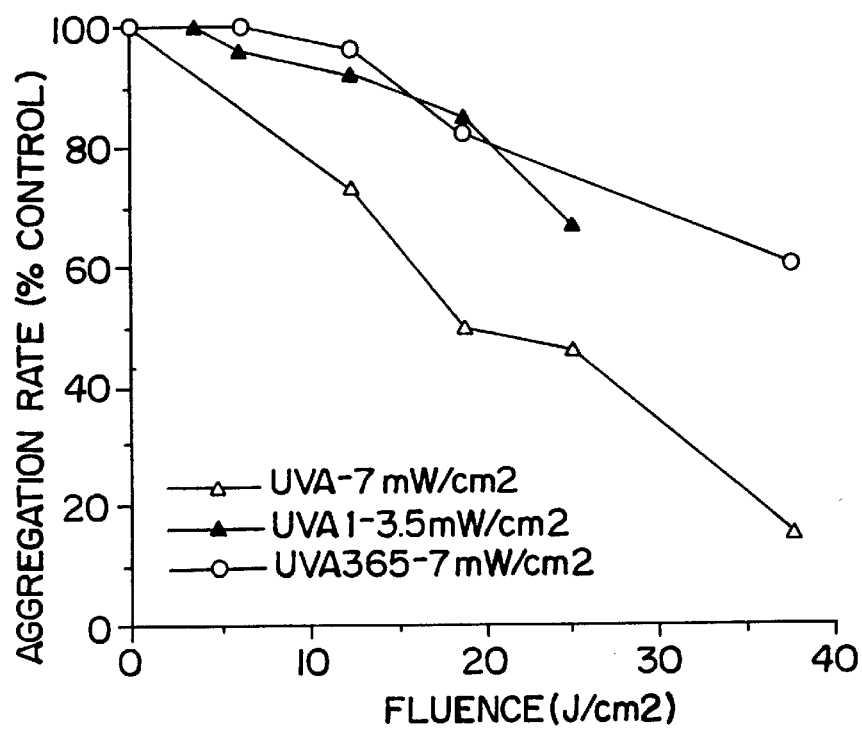
FIG. 3 is a graph depicting the effects of UVA irradiance and wavelength on function of PUVA treated PCs: PCs treated with UVA (320–400 nm) at 7 mW/cm$^2$ (open triangle) or UVA1 (345–400 nm) at 3.5 mW/cm$^2$ (filled triangle) as in FIG. 1, or with 7 mW/cm$^2$ of 360–370 nm (open circle) (UVP Model #B100A, Thomas Scientific, Swedesboro N.J.) from a mercury flood bulb UVA light source (UVP).
Figure 4A:
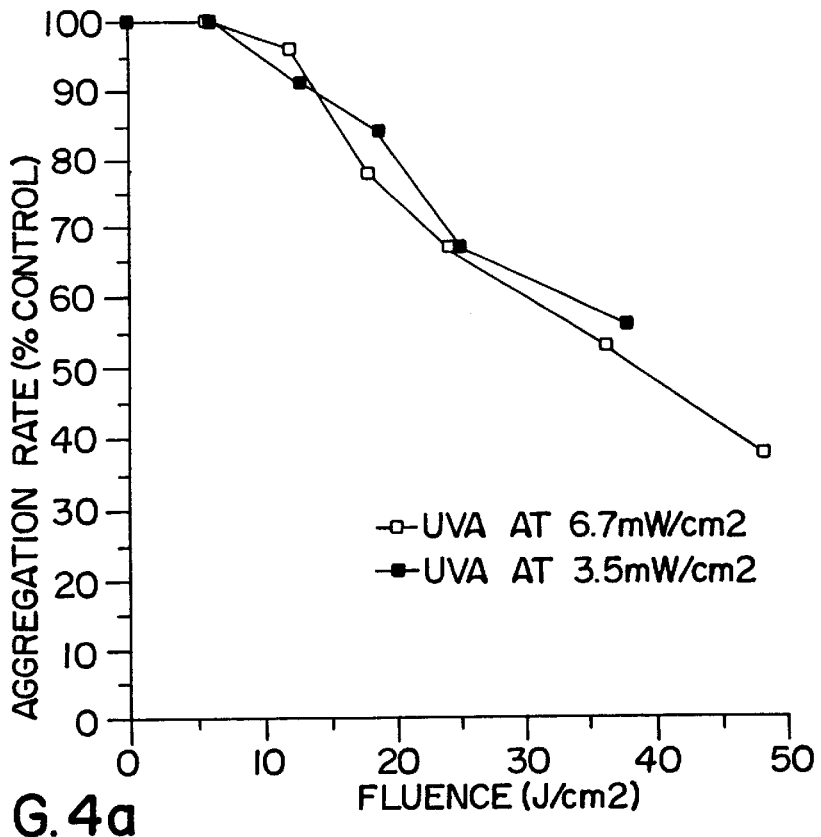
FIG. 4 comprises two graphs depicting the effects of irradiance (fluence rate) on virus kill (FIG. 4b) and platelet function (FIG. 4a): Treatment was with 50 μg/ml AMT, 0.35 mM rutin and UVA (320–400 nm; as in FIG. 1) at two different irradiances (i.e., 7 mW/cm$^2$ open squares or 3.5 mW/cm$^2$ filled squares). Irradiance was lowered by increasing the distance between sample and lamp.
Figure 4B:
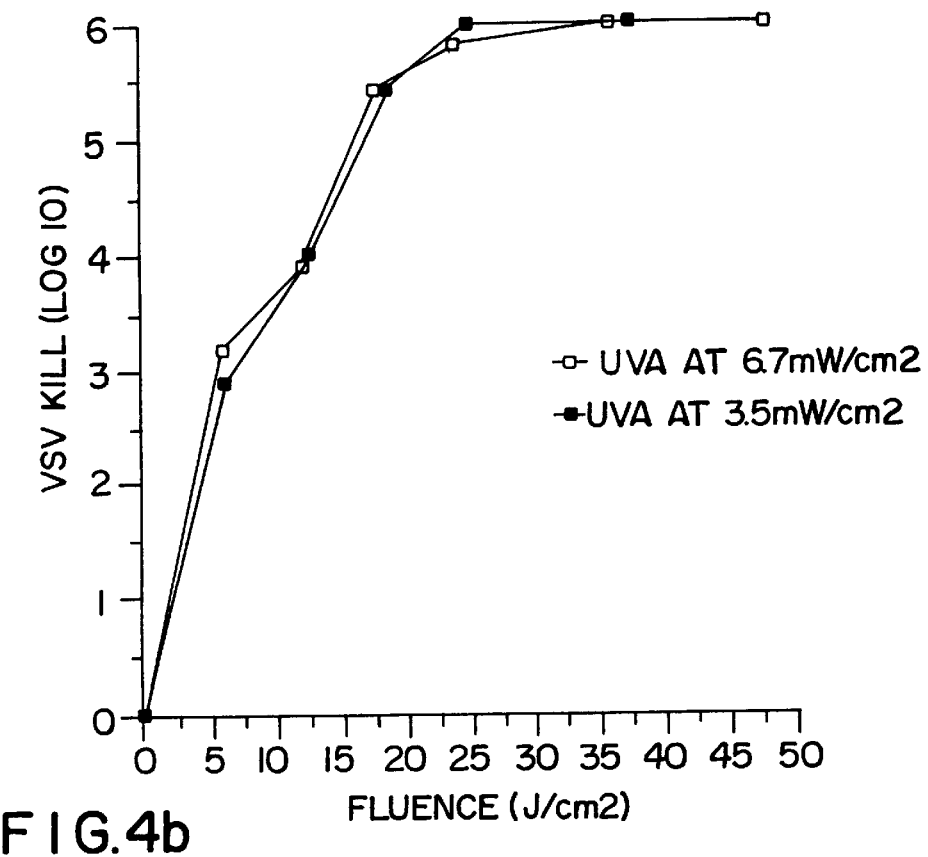

The improvement in platelet aggregation response when shorter wavelengths were excluded during PUVA treatment (see FIG. 3) was not just an effect of a lower fluence rate (see FIG. 4). With a UVA1 source having a steep emission peak near 365 nm (UVA 365) and a high (6.7 $mW/cm^2$) irradiance results were similar to those with UVA1 at a low irradiance (3.5 m $W/cm^2$) (FIG. 3). Maintenance of platelet function was dependent on the spectral emission of the UVA radiation source (FIG. 3) rather than on its intensity (FIG. 4).

Collectively, these data show that relatively more damage to platelets is caused by the shorter UVA wavelength range (<345 nm), and that UVA dose appropriate for PC treatment is therefore somewhat dependent on irradiator emmission spectrum. They also suggest that virus specificity of PUVA treatment of PCs can be enhanced by removal of UVA wavelengths below 345 nm.

It will be appreciated that the instant specification is set forth by way of illustration and not limitation, and that various modifications and changes may be made without departing from the spirit and scope of the present invention.

What is claimed is:

1. A process for treating a biological composition to inactivate an extracellular or intracellular virus that may be present therein, said process comprising performing two viral inactivation methods on said biological composition, wherein one of said two methods comprises the steps of: adding to the biological composition an irradiation sensitizer and then subjecting the resultant composition to a virucidally effective amount of UVA1 irradiation in the absence of UVA2 radiation and wherein the second viral inactivation method is selected from the group consisting of treatment with a solvent and a detergent, and a heat treatment.

2. The process according to claim 1, wherein the irradiation sensitizer is a psoralen.

3. The process according to claim 2, wherein the psoralen is 4'-aminomethyl-4,5',8-trimethyl psoralen.

4. The process according to claim 1, wherein the biological composition contains red blood cells or platelets.

5. The process according to claim 4, wherein the irradiation sensitizer is a psoralen.

6. The process according to claim 5, wherein the psoralen is 4'-aminomethyl-4,5',8-trimethyl psoralen.

7. The process according to claim 1, wherein a quencher is added to said biological composition before said biological composition is subjected to said UVA1 irradiation.

8. The process according to claim 7, wherein said quencher is selected from the group consisting of (a) a mixture of one or more compounds that quench type I photodynamic reactions and one or more compounds that quench type II photodynamic reactions or (b) a bifunctional compound which quenches both type I and type II reactions or (c) a mixture of a bifunctional compound that is capable of quenching both type I and type II reactions and an additional quencher which quenches either type I, type II or both type I and type II reactions.

9. The process according to claim 8, wherein the quencher is a bifunctional compound.

10. The process according to claim 9, wherein the bifunctional compound is selected from the group consisting of quercetin, chrysin, cachetin, rutin, hesperidin and naringen.

11. The process according to claim 10, wherein the biological composition contains red blood cells or platelets.

12. The process according to claim 1, wherein the other viral inactivation method comprises treatment with a solvent and a detergent.

13. The process according to claim 1, wherein the other viral inactivation method comprises heat treatment.

* * * * *